United States Patent
Ogawa et al.

(10) Patent No.: US 7,332,452 B2
(45) Date of Patent: *Feb. 19, 2008

(54) CAO-SIO₂-BASED BIOACTIVE GLASS AND SINTERED CALCIUM PHOSPHATE USING SAME

(75) Inventors: Tetsuro Ogawa, Tokyo (JP); Tadashi Kokubo, 50, Umegoako 2-chome, Nagaokakyo-shi, Kyoto (JP)

(73) Assignees: PENTAX Corporation, Tokyo (JP); Tadashi Kokubo, Kyoto (JP)

( * ) Notice: Subject to any disclaimer, the term of this patent is extended or adjusted under 35 U.S.C. 154(b) by 29 days.

This patent is subject to a terminal disclaimer.

(21) Appl. No.: 10/618,687

(22) Filed: Jul. 15, 2003

(65) Prior Publication Data

US 2004/0087429 A1    May 6, 2004

(30) Foreign Application Priority Data

Jul. 15, 2002    (JP) ............................... 2002-206319

(51) Int. Cl.
*C04B 35/447* (2006.01)
*C03C 3/078* (2006.01)
*A61K 33/42* (2006.01)

(52) U.S. Cl. ............................. 501/1; 501/57; 501/58; 501/72; 501/32

(58) Field of Classification Search .................... 501/1, 501/57, 58, 72, 5, 32; 424/602; 623/23.56
See application file for complete search history.

(56) References Cited

U.S. PATENT DOCUMENTS

| | | | |
|---|---|---|---|
| 3,981,736 A | | 9/1976 | Broemer et al. |
| 4,135,935 A | * | 1/1979 | Pfeil et al. ..................... 106/35 |
| 4,329,113 A | | 5/1982 | Ayache et al. |
| 4,437,192 A | * | 3/1984 | Fujiu et al. ............... 623/23.56 |
| 4,443,550 A | * | 4/1984 | Kume et al. ................... 501/65 |
| 4,497,629 A | | 2/1985 | Ogino et al. |
| 4,652,534 A | | 3/1987 | Kasuga |
| 4,708,652 A | * | 11/1987 | Fujiu et al. ............... 433/201.1 |
| 4,731,394 A | | 3/1988 | Vogel et al. |
| 4,783,429 A | | 11/1988 | Shibuya et al. |
| 4,783,550 A | * | 11/1988 | DiCosimo et al. .......... 560/145 |
| 4,871,384 A | | 10/1989 | Kasuga |
| 5,120,340 A | * | 6/1992 | Ducheyne et al. ........... 65/17.5 |
| 5,125,971 A | | 6/1992 | Nonami et al. |

(Continued)

FOREIGN PATENT DOCUMENTS

DE    247574    9/1983

(Continued)

OTHER PUBLICATIONS

English Language Translation of JP Appln. No. 2000-72572.

(Continued)

*Primary Examiner*—Karl E Group
(74) *Attorney, Agent, or Firm*—Greenblum & Bernstein, P.L.C.

(57) ABSTRACT

A bioactive glass having a composition substantially comprising 30 to 60 mol % of CaO, 40 to 70 mol % of SiO₂ and 20 mol % or less of Na₂O has low glass transition temperature and/or crystallization temperature, and a sintered calcium phosphate obtained by using the bioactive glass as a sintering aid has excellent biocompatibility, mechanical strength and sinterability.

14 Claims, 6 Drawing Sheets

U.S. PATENT DOCUMENTS

| | | | |
|---|---|---|---|
| 5,232,878 A | 8/1993 | Kasuga et al. | |
| 5,336,642 A | 8/1994 | Wolcott | |
| 5,344,456 A | 9/1994 | Nonami et al. | |
| 5,356,436 A | 10/1994 | Nonami et al. | |
| 5,634,956 A * | 6/1997 | Suh et al. | 65/33.1 |
| 5,658,332 A * | 8/1997 | Ducheyne et al. | 128/898 |
| 5,948,129 A | 9/1999 | Nonami et al. | |
| 5,981,412 A * | 11/1999 | Hench et al. | 501/5 |
| 6,130,178 A | 10/2000 | Andrus et al. | |
| 6,228,386 B1 * | 5/2001 | Yang | 424/426 |
| 6,306,785 B1 | 10/2001 | Nonami et al. | |
| 6,482,427 B2 * | 11/2002 | Yang | 424/426 |
| 6,875,715 B2 | 4/2005 | Nishikawa et al. | |
| 7,148,163 B2 * | 12/2006 | Berger et al. | 501/1 |
| 7,214,635 B2 * | 5/2007 | Gonda et al. | 501/1 |
| 2004/0235637 A1 * | 11/2004 | Berger et al. | 501/72 |
| 2005/0009682 A1 * | 1/2005 | Zimmer et al. | 501/5 |

FOREIGN PATENT DOCUMENTS

| | | | |
|---|---|---|---|
| EP | 0577342 | * | 1/1994 |
| EP | 1434742 | | 4/2003 |
| GB | 1441082 | | 6/1976 |
| GB | 2080281 | | 2/1982 |
| JP | 60-161368 | | 8/1985 |
| JP | 60-239341 | | 11/1985 |
| JP | 60239341 | | 11/1985 |
| JP | 61-197463 | | 9/1986 |
| JP | 61-205637 | * | 9/1986 |
| JP | 62-052163 | | 3/1987 |
| JP | 63242944 | | 10/1988 |
| JP | 3-37171 | | 2/1991 |
| JP | 3-090152 | | 4/1991 |
| JP | 4-036107 | | 2/1992 |
| JP | 5-105463 | | 4/1993 |
| JP | 06-030984 | | 2/1994 |
| JP | 6-22574 | | 3/1994 |
| JP | 7-232930 | | 9/1995 |
| JP | 10-067627 | | 3/1998 |
| JP | 2898331 | | 3/1999 |
| JP | 2934090 | | 5/1999 |
| JP | 200072572 | | 3/2000 |
| JP | 2001-130927 | | 5/2001 |
| JP | 3308355 | | 5/2002 |
| WO | 94/04657 | | 3/1994 |
| WO | 03/018496 | | 3/2003 |
| WO | 03/031356 | | 4/2003 |
| WO | 03/062163 | | 7/2003 |

OTHER PUBLICATIONS

English Language Abstract of JP Appln. No. 60-239341.

Salinas et al., "In vitro bioactivity of glass and glass-ceramics of the $3CaO \cdot P_2O_5$-$CaO \cdot SiO_2$-$CaO \cdot MgO \cdot 2SiO_2$ system", Biomaterials 21 (2000) 251-257.

Santos et al., "Liquid phase sintering of hydroxyapatite by phosphate and silicate glass additions:structure and properties of the composites", Journal of Materials Science: Materials in Medicine 6 (1995) 348-352.

Santos et al., Reinforcement of hydroxyapatite by adding $P_2O_5$-CaO glasses with $Na_2O,K_2O$ and MgO, Journal of Materials Science: Materials in Medicine 7 (1996) 187-189.

Leonor et al., "Novel starch thermoplastic/Bioglass® composites:Mechanical properties, degradation behavior and in-vitro bioactivity", Journal of Materials Science:Materials in Medicine 13 (2002) 939-945.

English Language Abstract of JP 63-242944.

English Language Abstract of DD 0247574.

English Language Abstract of JP 10-067627, published Mar. 10, 1998.

English Language Abstract of JP 06-030984, published Feb. 8, 1994.

English Language Abstract of JP 2001-130927, published May 15, 2001.

English Language Abstract of JP 61-197463, published Sep. 1, 1986.

English language abstract of JP 5-105463.

English Language Abstract of JP 2001-130927.

* cited by examiner

Fig. 3(a)
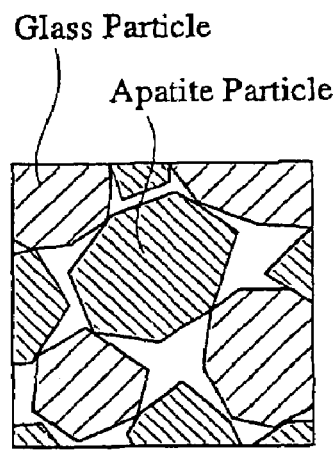
Glass Particle
Apatite Particle
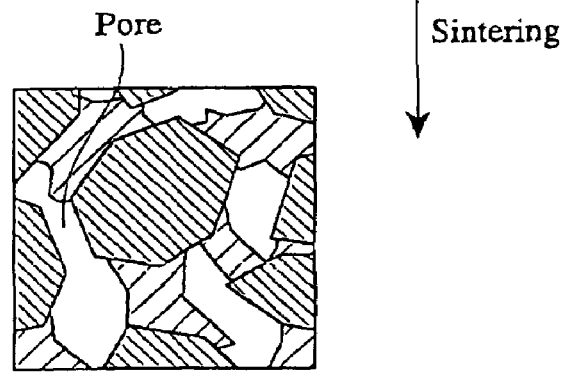
Fig. 3(b)
Pore
Sintering
Fig. 3(c)
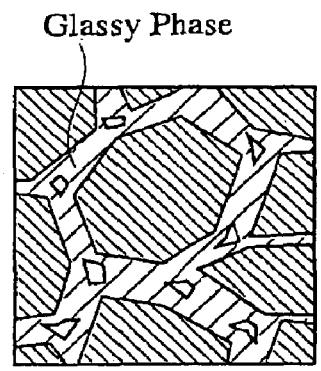
Glassy Phase
Fig. 3(d)
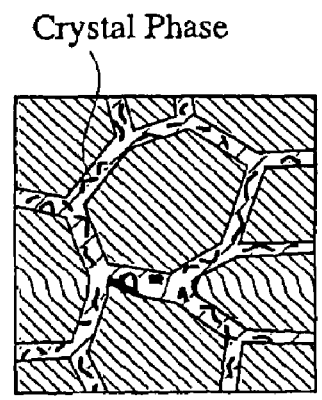
Crystal Phase

CAO-SIO₂-BASED BIOACTIVE GLASS AND SINTERED CALCIUM PHOSPHATE USING SAME

FIELD OF THE INVENTION

The present invention relates to a $CaO$—$SiO_2$-based bioactive glass usable in bone restoration materials such as artificial joints, artificial dental roots and artificial bones, and a sintered calcium phosphate using the bioactive glass.

BACKGROUND OF THE INVENTION

When an artificial material is implanted in a damaged region of a living body, the material is generally surrounded by, membranes of collagen fibers and thus isolated from neighboring bones. However, there have been known some artificial materials, which are not isolated by such fibrous membranes and strongly connect to bones in a living body. Examples of such artificial materials include $Na_2O$—$CaO$—$SiO_2$—$P_2O_5$-based bioglasses, sintered hydroxyapatite $Ca_{10}(PO_4)_6(OH)_2$, and crystallized glasses. Known as the crystallized glasses are, for example, $CaO$—$MgO$—$SiO_2$—$P_2O_5$-based bioactive glasses containing wollastonite crystals and apatite crystals such as hydroxyapatite crystals. These materials are referred to as bioactive ceramics, and some of them have put into practical use as important bone restoration materials.

The sintered hydroxyapatites have been widely used in medical treatments as bone restoration materials with high biocompatibility, and production methods thereof have been widely studied. With demand for more biocompatible artificial bones, etc. increasing in recent years, however, it is desired to develop bioactive ceramics containing a carbonated apatite, a component of a bone in living body.

Because the carbonated apatites are lower in decomposition temperature than the hydroxyapatites, sintering is carried out at relatively low temperatures to provide carbonated apatite ceramics. JP 2000-72572 A discloses a molded implant produced by plastically working a sintered apatite body, and a method for producing the molded implant, which comprises the steps of sintering an apatite at 900° C. or lower, filling the sintered apatite in a predetermined mold, and plastically working the sintered apatite at 300 to 780° C. In this method, because the sintering temperature is low, a carbonated or fluorinated apatite with low decomposition temperature can be used to produce the implant having high biocompatibility. However, this implant mainly comprises the apatite without other crystal phases, thereby having low mechanical strength.

The use of glass as a sintering aid is known to increase the mechanical strength of the bone restoration ceramic material composed of the apatite such as the carbonated apatite. In the sintering process, the glass is softened around main crystals of the apatite, and crystals are generated between the main crystals to be sintered, whereby the mechanical strength of the sintered apatite glass is increased. Conventionally, non-bioactive glasses are used as the sintering aid of the sintered hydroxyapatite body. However, because such non-bioactive glasses have high glass transition temperatures and/or crystallization temperatures, they cannot generate preferable crystals by sintering at temperatures lower than the decomposition temperatures of the carbonated apatites. Thus, the sintered carbonated apatite bodies using the non-bioactive glasses as sintering aids are not sufficient in the mechanical strength.

OBJECT OF THE INVENTION

Accordingly, an object of the present invention is to provide a bioactive glass low in a glass transition temperature and/or a crystallization temperature, and a sintered calcium phosphate that uses the bioactive glass to have high biocompatibility and mechanical strength.

SUMMARY OF THE INVENTION

As a result of intensive research in view of the above object, the inventors have found that a bioactive glass comprising 30 to 60 mol % of CaO, 40 to 70 mol % of $SiO_2$ and 20 mol % or less of $Na_2O$ is low in a glass transition temperature and/or a crystallization temperature, and that a sintered calcium phosphate using the bioactive glass as a sintering aid is excellent in biocompatibility and mechanical strength. The present invention has been completed based on the findings.

Thus, the bioactive glass of the present invention has a composition substantially comprising 30 to 60 mol % of CaO, 40 to 70 mol % of $SiO_2$, and 20 mol % or less of $Na_2O$.

It is preferred that the bioactive glass of the present invention further comprises $CaF_2$ and/or $B_2O_3$. The bioactive glass preferably has a glass transition temperature of 790° C. or lower. The difference between the glass transition temperature and the crystallization initiation temperature of the bioactive glass is preferably 80° C. or more. The bioactive glass preferably forms a β-wollastonite crystal when crystallized.

In a preferred embodiment, the bioactive glass has a composition substantially comprising 30 to 60 mol % of CaO, 40 to 70 mol % of $SiO_2$, and at least one of $Na_2O$, $CaF_2$ and $B_2O_3$, $Na_2O$ being 20 mol % or less, $CaF_2$ being 1 mol %, and $B_2O_3$ being 5 mol % or less. The bioactive glass is preferably substantially free from $P_2O_5$.

The sintered calcium phosphate glass of the present invention comprises the bioactive glass of the present invention as a sintering aid.

A calcium phosphate contained in the sintered calcium phosphate of the present invention is preferably a hydroxyapatite, a carbonated apatite or tricalcium phosphate.

BRIEF DESCRIPTION OF THE DRAWINGS

FIGS. 3(a) to 3(d) are schematic, cross-sectional views showing the changes of particle boundaries in the process of sintering a green body composed of hydroxyapatite particles and $CaO$—$SiO_2$-based glass particles, wherein FIG. 3(a) shows the hydroxyapatite particles and the $CaO$—$SiO_2$-based glass particles at a temperature lower than a glass transition temperature, FIG. 3(b) shows the particles immediately after the temperature reaches the glass transition temperature, FIG. 3(c) shows densification by sintering with the formation of a grain boundary phase (glassy phase), and FIG. 3(d) shows the formation of β-wollastonite crystals after the temperature reaches a crystallization temperature;

FIGS. 4(a) and 4(b) are graphs showing the results of X-ray structure analysis, wherein FIG. 4(a) shows the results of the bioactive glasses of Examples 1 to 6, and FIG. 4(b) shows the results of the bioactive glasses of Comparative Examples 1 to 5;

DETAILED DESCRIPTION OF THE PREFERRED EMBODIMENTS

[1] Bioactive Glass

Figure 1:
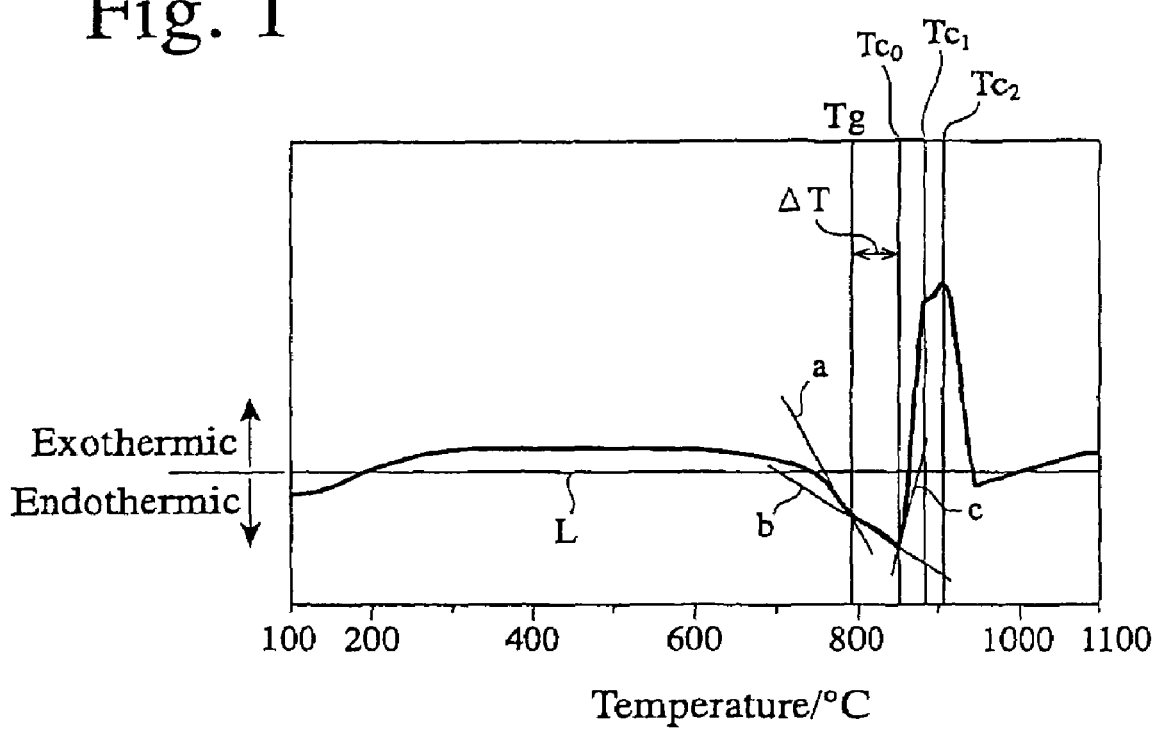
FIG. 1 is a graph showing the result of differential thermal analysis of a $CaO$—$SiO_2$-based glass.

The bioactive glass of the present invention has a composition substantially comprising 30 to 60 mol % of CaO, 40 to 70 mol % of $SiO_2$, and 20 mol % or less of $Na_2O$, and more preferably has a composition substantially comprising 40 to 50 mol % of CaO, 40 to 50 mol % of $SiO_2$, and 20 mol % or less of $Na_2O$. The glass with such a composition has bioactivity preferable for use as a bioactive material, and has mechanical strength, sinterability, etc. preferable for use as a sintering aid in a sintered calcium phosphate.

The bioactive glass comprising CaO releases calcium ions in a living body, thereby showing bioactivity. The bioactive glass, which has lost part of the calcium ions by elution, forms a silica gel layer mainly composed of silicon oxide. The silica gel layer forms the basis of nucleation of calcium phosphate crystals, whereby the bioactive glass can strongly connect to cortical bones.

The bioactive glass of the present invention comprises CaO and $SiO_2$ as main components with approximately equal molar ratios. Thus, the composition of the bioactive glass is substantially the same as that of the β-wollastonite, whereby the bioactive glass easily generates β-wollastonite crystals at a crystallization temperature. The crystal generated at the crystallization temperature is preferably a β-wollastonite crystal having a needle-like structure, because the mechanical strength of the sintered calcium phosphate glass is more increased by such a β-wollastonite crystal as compared with other crystals. In the case of adding a large amount of $P_2O_5$ to improve biocompatibility by conventional methods, however, the formation of the β-wollastonite crystal is often prevented at a crystallization temperature.

The bioactive glass of the present invention has improved biocompatibility with increased CaO content, needing no $P_2O_5$. In addition, because the glass transition temperature and/or the crystallization temperature of the bioactive glass are often increased by $P_2O_5$, the bioactive glass of the present invention is thus substantially free from $P_2O_5$. The bioactive glass of the present invention containing substantially no $P_2O_5$ easily generates the β-wollastonite crystal.

In the bioactive glass of the present invention, the total molar ratio of CaO and $SiO_2$ is preferably 90 mol % or more, more preferably 95 mol % or more.

Crystals of tricalcium phosphate $Ca_3(PO_4)_2$ may be generated at the crystallization temperature. Tricalcium phosphate is similar in physical properties, solubility and biocompatibility, to hydroxyapatites. Further, the crystal of tricalcium phosphate can improve the biocompatibility of the sintered calcium phosphate.

The sinterability is improved in a case where the sintering aid of the bioactive glass has (1) a low glass transition temperature Tg, (2) a crystallization initiation temperature $Tc_0$ remarkably lower than a decomposition temperature of calcium phosphate, and (3) a large difference ΔT between the glass transition temperature and the crystallization initiation temperature $Tc_0$. In the present invention, the term "crystallization initiation temperature" means a temperature at which the bioactive glass begins to generate a crystal such as the β-wollastonite crystal. Specifically, the crystallization initiation temperature is defined as a temperature of intersection of a base line and a bottom of an exothermic peak in a differential thermal analysis curve. The term "crystallization temperature" means a temperature at which the crystal is generated, with a definition as a temperature of an exothermic peak in a differential thermal analysis curve.

To evaluate the effects of $Na_2O$, etc. in a system of CaO, $SiO_2$ and $Na_2O$ on the glass transition temperature, etc., a bioactive glass composed of 50 mol % of CaO and 50 mol % of $SiO_2$ is hereinafter used as a control.

The graph of FIG. 1 shows the exothermic and endothermic changes with temperature in the differential thermal analysis of a bioactive glass composed of 50 mol % of CaO and 50 mol % of $SiO_2$ from 100° C. to 1100° C. The bioactive glass generates heat in a temperature range where the curve is above the line L, and absorbs heat in a temperature range where the curve is below the line L. A tangential line a at the inflection point of the curve at the beginning of heat absorption, an approximate line b (base line), and a tangential line c at the inflection point of the curve in the rising of an exothermic peak are given to the differential thermal analysis curve in the temperature range showing the endothermic changes. The glass transition temperature Tg is obtained from the intersection of the tangential line a and the approximate line b, and the crystallization initiation temperature $Tc_0$ is obtained from the intersection of the approximate line b and the tangential line c. In FIG. 1, each of $Tc_1$ and $Tc_2$ represents the crystallization temperature, and ΔT represents the difference of the glass transition temperature Tg and the crystallization initiation temperature $Tc_0$. The bioactive glass shows a softening behavior in a temperature region between the glass transition temperature Tg and the crystallization initiation temperature $Tc_0$.

The bioactive glass with a low glass transition temperature Tg can be used as a sintering aid for the carbonated apatite, etc. having a low decomposition temperature. To easily sinter the bioactive glass at a temperature lower than the decomposition temperature of calcium phosphate and higher than the crystallization initiation temperature $Tc_0$, the crystallization initiation temperature $Tc_0$ is preferably lower than the decomposition temperature with a difference of approximately 400° C. or more. The glass transition temperature Tg is preferably 790° C. or lower, more preferably 770° C. or lower. Further, the bioactive glass of the present invention preferably has a large difference ΔT between the glass transition temperature and the crystallization initiation temperature. When the difference ΔT is large, dense crystals are easily obtained without needing precise control of the sintering temperature. The difference ΔT of the bioactive glass is preferably 80° C. or more, more preferably 90° C. or more.

The glass transition temperature Tg of the bioactive glass may be lowered by adding $Na_2O$. However, an excess amount of $Na_2O$ often inhibits the formation of the β-wollastonite crystal. Thus, the amount of $Na_2O$ is preferably 10 mol % or less, more preferably 5 mol % or less, particularly preferably 1 mol % or less. The lower limit of the amount of $Na_2O$ is preferably 0.1 mol %. When the amount of $Na_2O$ added is less than 0.1 mol %, the effects of adding $Na_2O$ are substantially not obtained.

The addition of $CaF_2$ to the bioactive glass can lower its glass transition temperature Tg and increase the difference $\Delta T$. With $CaF_2$ added, the glass transition temperature Tg and the crystallization initiation temperature $Tc_0$ are both lowered, and the reduction of the crystallization initiation temperature $Tc_0$ is smaller than that of the glass transition temperature Tg. Thus, the glass transition temperature Tg is lowered, and the difference $\Delta T$ is increased. The amount of $CaF_2$ added is preferably 1 mol % or less, more preferably 0.5 mol % or less.

$B_2O_3$ may be added to the bioactive glass. The addition of a small amount of $B_2O_3$ can lower its glass transition temperature Tg and crystallization initiation temperature $Tc_0$ and increase the difference $\Delta T$ like the addition of $CaF_2$. The amount of $B_2O_3$ added is preferably 5 mol % or less, more preferably 1 mol % or less.

At least one of $Na_2O$, $CaF_2$ and $B_2O_3$ should be contained in the bioactive glass of the present invention. It is preferable that $Na_2O$, $CaF_2$ and $B_2O_3$ are added to the bioactive glass in combination. The bioactive glass with the preferred glass transition temperature Tg and the preferred difference $\Delta T$ can be obtained by appropriately combining $Na_2O$, $CaF_2$ and $B_2O_3$. The total amount of $Na_2O$, $CaF_2$ and $B_2O_3$ is preferably 5 mol % or less, more preferably 2 mol % or less. The lower limit of the total amount of $Na_2O$, $CaF_2$ and $B_2O_3$ is preferably 0.1 mol %.

An inorganic compound such as $K_2O$, $Li_2O$, $TiO_2$, $Al_2O_3$, MgO and $ZrO_2$ may be added to the bioactive glass. It is preferable to use an inorganic compound that does not increase the glass transition temperature Tg and does not inhibit the formation of the β-wollastonite crystal.

There are no particular restrictions in a method for producing the bioactive glass of the present invention. The bioactive glass may be produced by a method described in JP 60-239341 A, etc. Specifically, powders of materials ($CaO$, $SiO_2$, $Na_2O$, $CaF_2$, $B_2O_3$, etc.) with a desired composition are put in a platinum crucible and heated at 1,200° C. to 1,600° C. for approximately 3 hours to obtain a molten glass. The molten glass is molded and annealed to produce the bioactive glass. Though not particularly restrictive, the shape of the bioactive glass may be selected in a shape of an ingot, a sphere, beads, particles, granules, etc. depending on the purposes. When the bioactive glass is used as a starting material for the sintered calcium phosphate of the present invention that will be described below, the diameter of the bioactive glass may be controlled by pulverization or classification.

[2] Sintered Calcium Phosphate (a) Composition of Sintered Calcium Phosphate

A calcium phosphate contained in the sintered calcium phosphate of the present invention is preferably a hydroxyapatite, a carbonated apatite or tricalcium phosphate.

When the hydroxyapatite is heated, it is gradually deprived of hydroxyl groups at around 1,000° C. or higher, causing decomposition at around 1,300° C. or higher. Thus, in the case of using the hydroxyapatite for the sintered calcium phosphate, the sintering process is preferably carried out at a temperature lower than 1,000° C.

The biocompatibility of the sintered calcium phosphate may be further increased by using the carbonated apatite. The carbonate moieties of the carbonated apatite are eliminated at a temperature of around 900° C. or higher, which is lower than the elimination temperature of the hydroxyl groups of the hydroxyapatite. Thus, in the case of using the carbonated apatite for the sintered calcium phosphate, the sintering process is preferably carried out at a temperature lower than 900° C.

Figure 2:
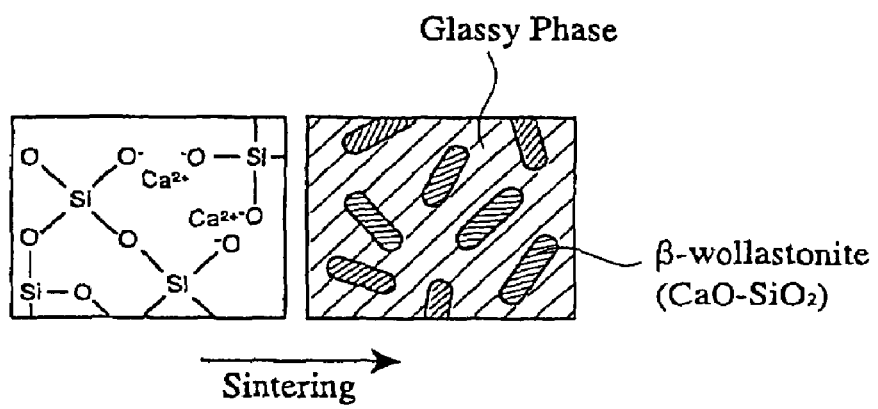
FIG. 2 is a schematic view showing the formation of β-wollastonite crystals in the process of sintering a $CaO$—$SiO_2$-based glass.

The sintered calcium phosphate of the present invention comprises the bioactive glass of the present invention as a sintering aid. The bioactive glass preferably generates the β-wollastonite crystals at the crystallization temperature as shown in FIG. 2. The percentage of the generated β-wollastonite crystals to the bioactive glass is preferably 10 to 100% by mass.

(b) Method for Producing Sintered Calcium Phosphate

The sintered calcium phosphate of the present invention may be produced by a common sintering method.

The average particle diameter of the calcium phosphate particles is preferably 1 to 100 μm, more preferably 10 to 20 μm. The calcium phosphate particles with such an average particle diameter may be prepared by a spray granulation method. Thus, the calcium phosphate particles are agglomerates of fine calcium phosphate crystals (primary particles). The calcium phosphate crystal is preferably in the form of nano-particles having diameters of 1 μm or less, more preferably nano-particles having diameters of 10 to 500 nm.

The pulverized particles of the bioactive glass of the present invention may be added to the calcium phosphate particles. The average particle diameter of the bioactive glass particles is preferably 0.1 to 10 μm, more preferably 5 μm or less. The percentage of the bioactive glass to the calcium phosphate particles is preferably 0.5 to 10% by mass, more preferably 1 to 5% by mass.

The calcium phosphate particles and the bioactive glass particles may be wet-blended with alumina balls and a solvent such as isopropyl alcohol, ethanol, etc., and dried to obtain a mixture for sintering. The drying time is preferably 0.5 to 5 hours, more preferably 2 to 5 hours. The mixture is preferably put in a stainless steel die, etc. and press-molded and then cold-isostatic-pressed.

A green body thus obtained is sintered. The sintering temperature of the green body is preferably 700 to 1300° C., more preferably 700 to 900° C. The sintering time is preferably 0.5 to 10 hours, more preferably 2 to 5 hours. The sintering process is described with reference to the schematic views of FIGS. 3(a) to 3(d). As shown in FIG. 3(a), the calcium phosphate particles and the glass particles are uniformly distributed in the green body. When the green body is heated at the glass transition temperature or higher, the glass particles are softened as shown in FIG. 3(b). When the green body is further heated, the softened glass particles penetrate into pores between the calcium phosphate particles to cause densification, thereby forming grain boundary phases (glassy phases) as shown in FIG. 3(c).

As shown in FIG. 3(d), when the sintering process proceeds and the green body is heated at a temperature at which at least part of the glass components forms crystals, crystals are generated in the grain boundary phase to form crystal phases. Because the sintering temperature is lower than the melting temperature and the decomposition temperature of the calcium phosphate throughout the sintering process, the calcium phosphate particles are hardly decomposed or dissolved in the glass. Thus, the crystals such as the β-wollastonite crystals of certain glass components are generated between the calcium phosphate crystals, to provide the sintered, dense calcium phosphate glass. The heating rate is preferably uniform, and preferred heating rate is approximately 10° C./min. The sintering temperature is preferably maintained between the glass transition temperature and the crystallization temperature for 1 to 5 hours. The sintered calcium phosphate is preferably cooled in a furnace.

The present invention will be explained in more detail with reference to Examples below without intention of restricting the scope of the present invention.

EXAMPLE 1

49.5 mol % of CaO powder, 49.5 mol % of $SiO_2$ powder, and 1 mol % of $Na_2O$ powder were mixed and melted at 1500° C. for 2 hours, to produce a bioactive glass ingot having a uniform composition.

EXAMPLES 2 TO 6

Material powders Were melted at 1500° C. for 2 hours, to produce bioactive glass ingots having uniform compositions shown in Table 1.

TABLE 1

| Bioactive Glass | Composition (mol %) | | | | |
|---|---|---|---|---|---|
| | CaO | $SiO_2$ | $Na_2O$ | $CaF_2$ | $B_2O_3$ |
| Example 1 | 49.5 | 49.5 | 1.0 | — | — |
| Example 2 | 47.5 | 47.5 | 5.0 | — | — |
| Example 3 | 40.0 | 50.0 | 10.0 | — | — |
| Example 4 | 49.5 | 50.0 | — | 0.5 | — |
| Example 5 | 49.0 | 49.5 | 1.0 | 0.5 | — |
| Example 6 | 49.5 | 49.0 | 1.0 | 0.5 | 1.0 |

COMPARATIVE EXAMPLES 1 TO 5

Material powders were melted at 1500° C. for 2 hours, to produce bioactive glass ingots having uniform compositions shown in Table 2.

TABLE 2

| Bioactive Glass | Composition (mol %) | | |
|---|---|---|---|
| | CaO | $SiO_2$ | $P_2O_5$ |
| Comparative Example 1 | 50.0 | 50.0 | — |
| Comparative Example 2 | 49.0 | 51.0 | — |
| Comparative Example 3 | 40.0 | 60.0 | — |
| Comparative Example 4 | 47.5 | 47.5 | 5.0 |
| Comparative Example 5 | 60.0 | 30.0 | 10.0 |

Each bioactive glass of Examples 1 to 6 and Comparative Examples 1 to 5 was subjected to differential thermal analysis, to obtain the glass transition temperature Tg, the crystallization initiation temperature $Tc_0$, the crystallization temperature Tc, and the difference ΔT between the glass transition temperature and the crystallization initiation temperature.

As shown in Table 3, each bioactive glass, of Examples 1 to 6 had a lower glass transition temperature Tg as compared with the bioactive glasses of Comparative Examples free of $Na_2O$, etc. Each bioactive glass of Examples 4 to 6 containing $CaF_2$ had a relatively large difference ΔT.

TABLE 3

| Bioactive Glass | Glass Transition Temperature Tg (° C.) | Crystallization Initiation Temperature $Tc_0$ (° C.) | Crystallization Temperature Tc (° C.) | Difference ΔT between Tg and $Tc_0$ (° C.) |
|---|---|---|---|---|
| Example 1 | 774.4 | 862.5 | 882.6 | 88.1 |
| Example 2 | 717.4 | 859.0 | 829.3 | 141.6 |
| Example 3 | 662.9 | 726.0 | 753.0 | 63.1 |
| | | | 814.3 | |
| | | | 918.2 | |
| Example 4 | 780.4 | 862.6 | 883.8 | 82.2 |
| Example 5 | 763.1 | 859.0 | 874.9 | 95.9 |
| Example 6 | 746.4 | 837.4 | 851.6 | 91.0 |
| | | | 869.4 | |
| Comparative Example 1 | 792.9 | 861.8 | 880.6 | 68.8 |
| | | | 914.7 | |
| Comparative Example 2 | 789.6 | 866.7 | 886.2 | 77.1 |
| Comparative Example 3 | 780.8 | 882.2 | 911.9 | 101.4 |
| Comparative Example 4 | 789.1 | 896.1 | 944.9 | 107.0 |
| Comparative Example 5 | 807.2 | 873.4 | 885.9 | 66.2 |

Figure 4A:
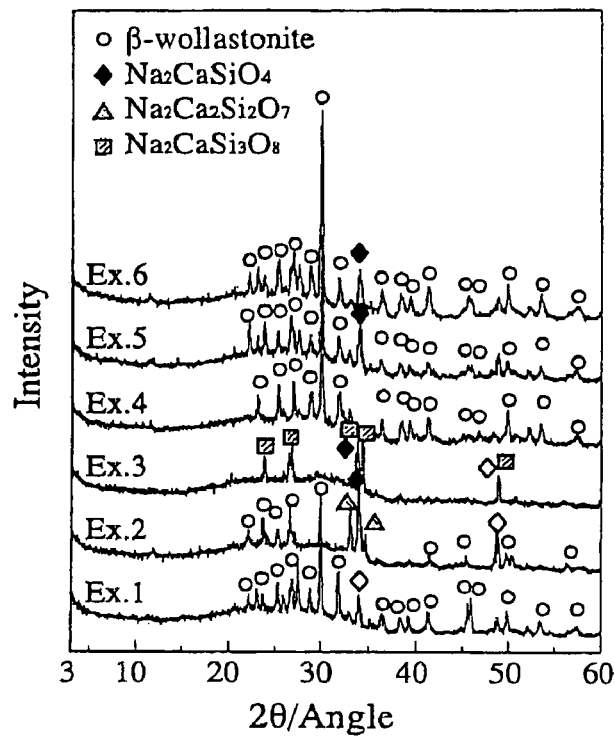
Figure 4B:
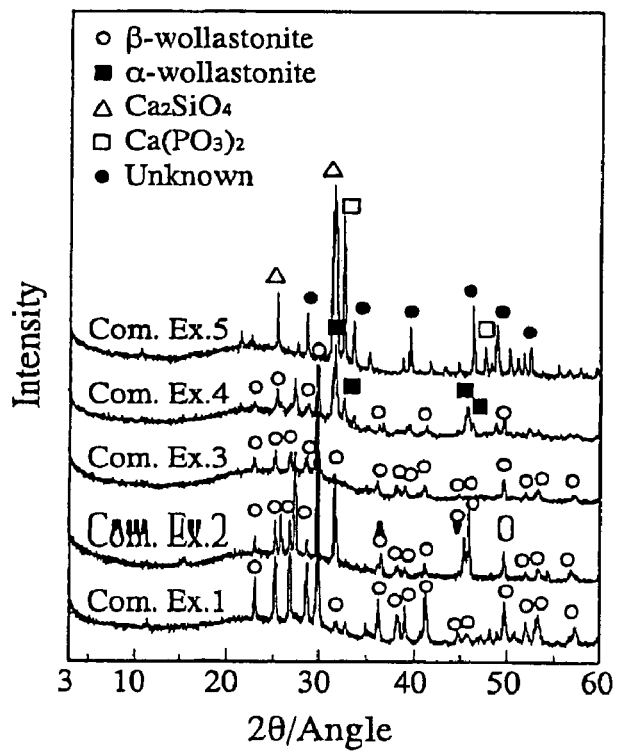

Each bioactive glass of Examples 1 to 6 and Comparative Examples 1 to 5 was heated at the crystallization temperature or higher, and the generated crystals were analyzed by X-ray structure analysis. The results of X-ray analysis of Examples 1 to 6 are shown in the graphs of FIG. 4(a), and the results of Comparative Examples 1 to 5 are shown in the graphs of FIG. 4(b).

As shown in Table 4, the β-wollastonite crystals were mainly generated in the bioactive glasses of Examples 1, 2, and 4 to 6, and Comparative Examples 1 to 3, which contained approximately the same molar amount of CaO and $SiO_2$. On the other hand, the β-wollastonite crystals were hardly generated in the bioactive glasses of Comparative Examples 4 and 5 containing $P_2O_5$.

TABLE 4

| Bioactive Glass | Crystallization Temperature Tc (° C.) | Crystal System |
|---|---|---|
| Example 1 | 882.6 | β-wollastonite >> $Na_2CaSiO_4$[1] |
| Example 2 | 829.3 | β-wollastonite > $Na_2CaSiO_4$, $Na_2Ca_2SiO_7$[2] |
| Example 3 | 753.0 | $Na_2CaSi_3O_8$ >> $Na_2CaSiO_4$ |
| | 814.3 | $Na_2CaSi_3O_8$ >> $Na_2CaSiO_4$ |
| | 918.2 | $Na_2CaSi_3O_8$ >> $Na_2CaSiO_4$ |
| Example 4 | 883.8 | β-wollastonite |
| Example 5 | 874.9 | β-wollastonite >> $Na_2CaSiO_4$ |
| Example 6 | 851.6 | $Na_2CaSiO_4$ > β-wollastonite |
| | 869.4 | β-wollastonite > $Na_2CaSiO_4$ |
| Comparative Example 1 | 880.6 | β-wollastonite |
| | 914.7 | β-wollastonite |
| Comparative Example 2 | 886.2 | β-wollastonite |
| Comparative Example 3 | 911.9 | β-wollastonite |
| Comparative Example 4 | 944.9 | α-wollastonite > β-wollastonite |
| Comparative Eample 5 | 885.9 | $Ca_2SiO_4$ > $Ca(PO_3)_2$ |

Notes:
[1] ">>" means that the crystal on the left side was generated in an extremely larger amount.
[2] ">" means that the crystal on the left side was generated in a larger amount.

EXAMPLE 7

Figure 5:
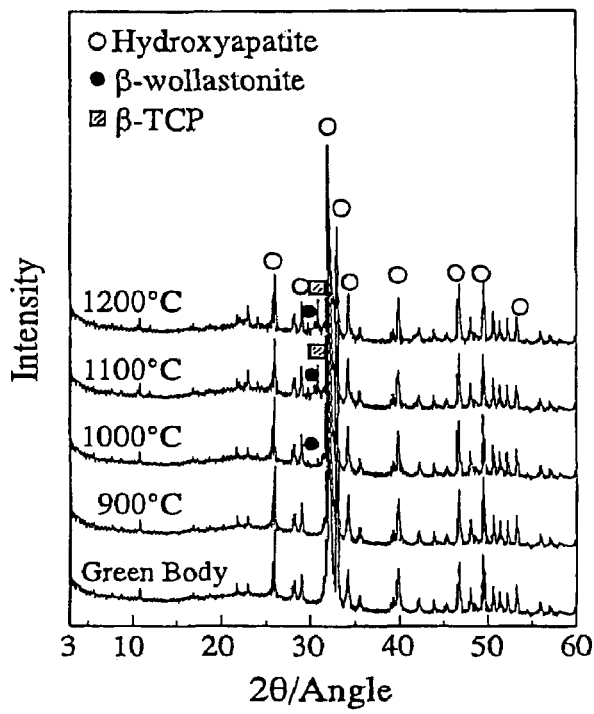
FIG. 5 is a graph showing the results of X-ray analysis of sintered calcium phosphate in Example 7.

The bioactive glass ingot of Example 1 was pulverized into particles with an average particle diameter of 10 µm, and 5% by mass thereof was added to 100% by mass of agglomerated particles (average diameter: 15 µm) of hydroxyapatite nano-particles available from Pentax Corporation. The resultant mixture was wet-blended using isopropyl alcohol and alumina balls, and dried to obtain powder for sintering. 0.2 g of the powder was placed in a stainless steel die, and press-molded and cold-isostatic-pressed (CIP), and finished to produce a disc-shaped green body having a diameter of 10 mm and thickness of 2 mm. The green body was sintered at 900° C. for 3 hours and cooled in a furnace to produce a sintered body of the hydroxyapatite glass. The heating rate in the sintering was 10° C./min. Further, three sintered bodies of the hydroxyapatite glass were produced in the same manner except for changing the sintering temperature to 1,000° C., 1100° C. or 1200° C., respectively. The sintered bodies and the unsintered green body were subjected to X-ray analysis. The results of the X-ray analysis are shown in the graph of FIG. 5.

EXAMPLE 8

Figure 6:
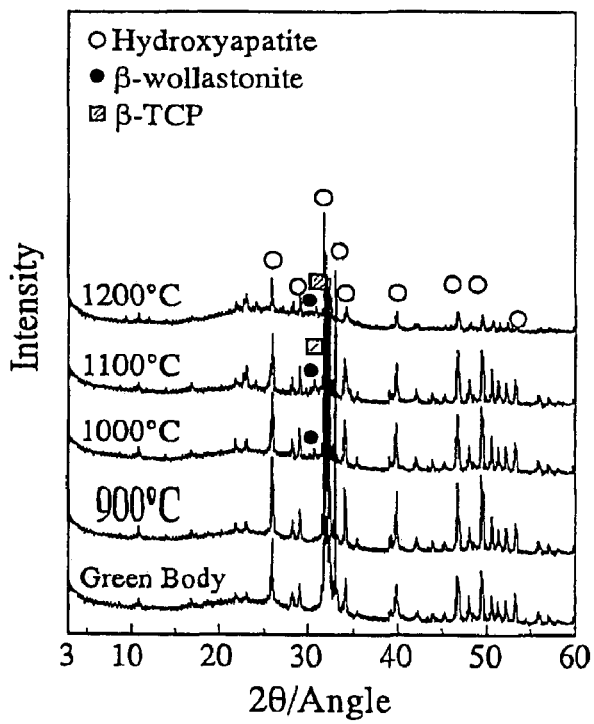
FIG. 6 is a graph showing the results of X-ray analysis of sintered calcium phosphate in Example 8.

Four sintered bodies of the same hydroxyapatite glass were produced by sintering at different temperatures in the same manner as in Example 7 except for using the bioactive glass of Example 5. The sintered bodies and the unsintered green body were subjected to X-ray analysis. The results of the X-ray analysis are shown in the graph of FIG. 6.

COMPARATIVE EXAMPLE 6

Figure 7:
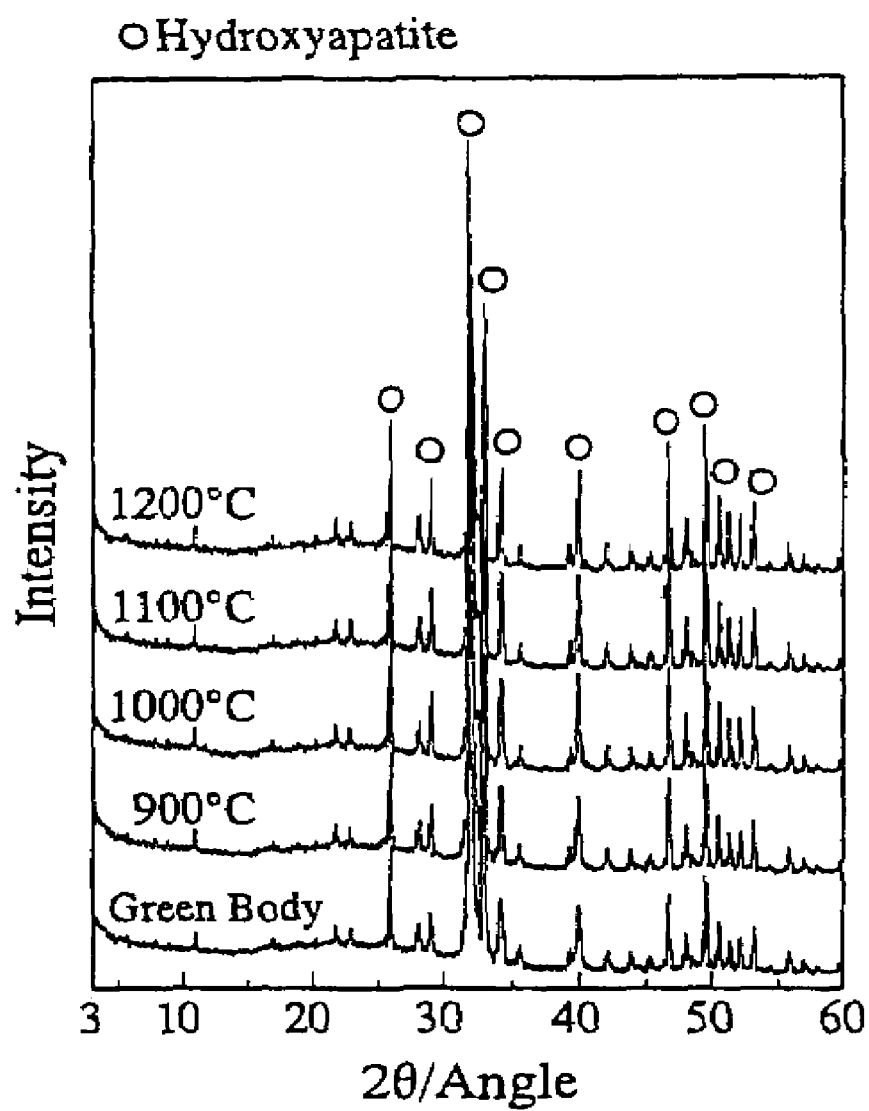
FIG. 7 is a graph showing the results of X-ray analysis of sintered hydroxyapatites in Comparative Example 6.

The hydroxyapatite green bodies in Examples 7 and 8 were sintered at 900° C., 1,000° C., 1,100° C. or 1,200° C., respectively, for 3 hours. The resultant sintered bodies and the unsintered green body were subjected to X-ray analysis. The results of the X-ray analysis are shown in the graph of FIG. 7.

In the case of Comparative Example 6, only peaks of the hydroxyapatite were detected irrespective of the sintering temperature. In the case of the sintered bodies of Examples 7 and 8, which contained the bioactive glasses, those sintered at 1,000° C. or higher showed peaks of the β-wollastonite, and those sintered at 1,100° C. or higher further showed peaks of β-tricalcium phosphate. The β-wollastonite phase is preferable for reinforcing the grain boundaries, and the β-tricalcium phosphate phase is preferable for enhancing bioactivity.

EXAMPLE 9

The bioactive glass produced in Example 5 were examined with respect to cell attachment, cell proliferation and alkaline phosphotase activity as follows: A test piece (5 mm×5 mm×2 mm) of the bioactive glass of Example 5 was subjected to high-pressure steam sterilization, and placed in a 24-well multiplate for cell culture (available from Sumitomo Bakelite Co., Ltd., diameter: 16.3 mm, base area: 1.8 $cm^3$). $1.0 \times 10^4$ HOS cells derived from human osteosarcoma (ATCC No. CRL-1543) were seeded in each plate, and 1 ml of D-MEM 10% FBS (available from GIBCO-BRL) was added to the plate. The cells were incubated at 37° C. for 60 minutes or 7 days in air with a 5-% $CO_2$ content. The culture medium was exchanged on the fourth day of the 7-days incubation.

COMPARATIVE EXAMPLE 7

HOS cells were incubated in the same manner as in Example 9 except for using a test piece (diameter: 6 mm×2 mm) of the sintered hydroxyapatite body of Comparative Example 6 (sintering temperature: 1,000° C.) instead of the bioactive glass as a carrier. The cell attachment, cell proliferation and alkaline phosphotase activity of the sintered hydroxyapatite body were examined.

The incubated cells were fixed by a 10-%, neutral, buffered formalin solution, stained by methylene blue, and observed by an optical microscope and an electron microscope. To evaluate cell differentiation, the incubated cells were homogenized and the alkaline phosphotase activity was measured by Alkalipha K-test Wako (available from Wako Pure Chemical Industries, Ltd.).

Figure 8:
FIG. 8 is a photomicrograph with a magnification of 200 of HOS cells incubated on the carrier of Example 9 for one week.
Figure 9:
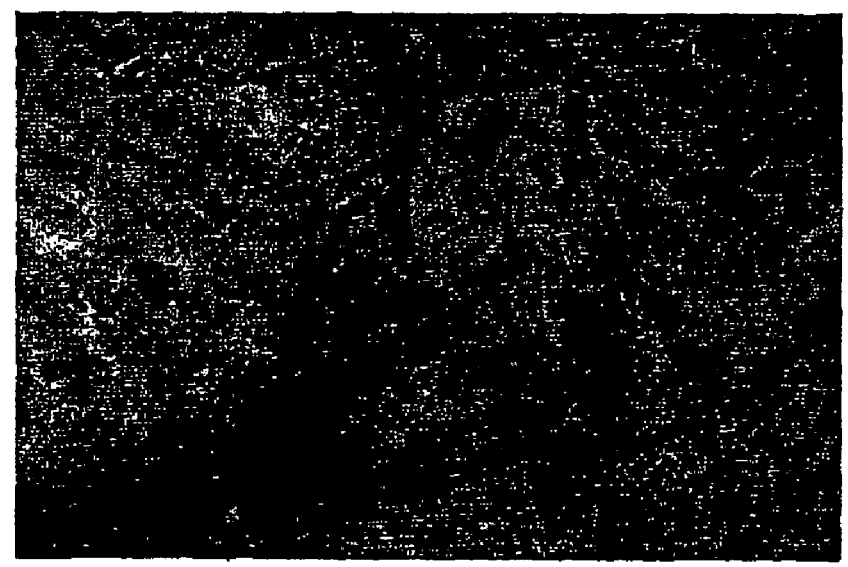
FIG. 9 is a photomicrograph with a magnification of 200 of HOS cells incubated on the carrier of Comparative Example 7 for one week.

Adhesion of the cells to each carrier used in Example 9 and Comparative Example 7 was observed after the 60-minute incubation. In the case of the carrier according to Example 9, the cells were proliferated on the bioactive glass, and were nearly in a confluent state on the fourth day of the incubation. After the 7-days incubation, the cells were proliferated on each carrier of Example 9 and Comparative Example 7 into a confluent state. Photomicrographs (a magnification of 200) of the HOS cells incubated for a week are shown in FIGS. 8 and 9. FIG. 8 shows the HOS cells incubated on the carrier of Example 9, and FIG. 9 shows the HOS cells incubated on the carrier of Comparative Example 7. Further, numbers of the cells, attached to the bioactive glass and the sintered hydroxyapatite body after the incubation of 60 minutes and 7 days, are shown in Table 5. The carrier of Example 9 provided excellent cell proliferation, as well as the carrier of Comparative Example 7.

TABLE 5

| | Number of Attached Cells Incubation Period | |
|---|---|---|
| Carrier | 60 minutes | 7 days |
| Example 9 | $6.8 \times 10^3/cm^2$ | $1.8 \times 10^5/cm^2$ |
| Comparative Example 7 | $6.0 \times 10^3/cm^2$ | $2.0 \times 10^5/cm^2$ |

The alkaline phosphotase activities after the incubation of 7 days are shown in Table 6. The carrier of Example 9 was higher in the alkaline phosphotase activity than the carrier of Comparative Example 7. This result indicates that the bioactive glass affects the cell differentiation.

TABLE 6

| Carrier | Alkaline Phosphotase Activity per 1 $cm^2$ (unit: K-A) |
|---|---|
| Example 9 | 2.4 |
| Comparative Example 7 | 1.1 |

As described in detail above, the bioactive glass of the present invention has a composition substantially comprising 30 to 60 mol % of CaO, 40 to 70 mol % of $SiO_2$ and 20 mol % or less of $Na_2O$. By containing CaO and $SiO_2$ as main components, the bioactive glass easily generates the β-wollastonite crystal at the crystallization temperature, resulting in excellent mechanical strength. By containing $Na_2O$, the bioactive glass has a low glass transition temperature and/or crystallization temperature. Further, when the bioactive glass of the present invention contains $CaF_2$ and/or $B_2O_3$, the difference between the glass transition temperature and the crystallization temperature is increased. The sintered calcium phosphate of the present invention comprises the bioactive glass as a sintering aid, thereby exhibiting high biocompatibility and excellent mechanical strength and sinterability. The present disclosure relates to subject matter contained in Japanese Patent Application No. 2002-206319 (filed on Jul. 15, 2002) which is expressly incorporated herein by reference in its entirety.

What is claimed is:

1. A sintered calcium phosphate comprising a bioactive glass as a sintering aid, said bioactive glass formed from a composition substantially comprising 30 to 60 mol % of CaO, 40 to 70 mol % of $SiO_2$, 20 mol % or less of $Na_2O$, and 0.1-1.0 mol % of $CaF_2$, said sintered calcium phosphate being excellent in cell attachment, cell proliferation and alkaline phosphotase activity, wherein said composition forming the bioactive glass is free from $P_2O_5$, and said sintered calcium phosphate is formed from a calcium phosphate comprising a hydroxyapatite, a carbonated apatite or tricalcium phosphate.

2. The sintered calcium phosphate according to claim 1, wherein said composition forming said bioactive glass further comprises $B_2O_3$.

3. The sintered calcium phosphate according to claim 1, wherein a difference between glass transition temperature and crystallization initiation temperature in said bioactive glass is 80° C. or more.

4. The sintered calcium phosphate according to claim 1, wherein the composition forming said bioactive glass comprises CaO and $SiO_2$ in approximately equal molar ratios.

5. The sintered calcium phosphate according to claim 1, wherein said bioactive glass generates a β-wollastonite crystal at a crystallization temperature.

6. A sintered calcium phosphate comprising a bioactive glass as a sintering aid, said bioactive glass formed from a composition substantially comprising 30 to 60 mol % of CaO, 40 to 70 mol % of $SiO_2$, 0.1-1 mol % of $CaF_2$, and at least one of $Na_2O$ and $B_2O_3$, $Na_2O$ being 20 mol % or less, and $B_2O_3$ being 5 mol % or less, said sintered calcium phosphate being excellent in cell attachment, cell proliferation and alkaline phosphotase activity, wherein said sintered calcium phosphate is formed from a calcium phosphate comprising a hydroxyapatite, a carbonated apatite or tricalcium phosphate.

7. The sintered calcium phosphate according to claim 6, wherein said composition forming said bioactive glass is free from $P_2O_5$.

8. A sintered calcium phosphate comprising a bioactive glass as a sintering aid, said bioactive glass formed from a composition consisting essentially of 30 to 60 mol % of CaO, 40 to 70 mol % of $SiO_2$, 0.1-5 mol % of $Na_2O$, and 0.1-1 mol % of $CaF_2$, wherein said sintered calcium phosphate is formed from a calcium phosphate comprising a hydroxyapatite, a carbonated apatite or tricalcium phosphate.

9. The sintered calcium phosphate according to claim 8, wherein a difference between glass transition temperature and crystallization initiation temperature in said bioactive glass is 80° C. or more.

10. The sintered calcium phosphate according to claim 8, wherein said composition forming said bioactive glass is free from $P_2O_5$.

11. The sintered calcium phosphate according to claim 8, wherein said bioactive glass generates a β-wollastonite crystal at a crystallization temperature.

12. A sintered calcium phosphate comprising a bioactive glass as a sintering aid, said bioactive glass formed from a composition consisting essentially of 30 to 60 mol % of CaO, 40 to 70 mol % of $SiO_2$, 0.1-5 mol % of $Na_2O$, and $B_2O_3$, said $B_2O_3$ being present in an amount of 5 mol % or less, wherein said sintered calcium phosphate is formed from a calcium phosphate comprising a hydroxyapatite, a carbonated apatite or tricalcium phosphate.

13. A sintered calcium phosphate comprising a bioactive glass as a sintering aid, said bioactive glass formed from a composition consisting essentially of 30 to 60 mol % of CaO, 40 to 70 mol % of $SiO_2$, and 0.1-5 mol % of $Na_2O$, said sintered calcium phosphate being excellent in cell attachment, cell proliferation and alkaline phosphotase activity, wherein said sintered calcium phosphate is formed from a calcium phosphate comprising a hydroxyapatite, a carbonated apatite or tricalcium phosphate, wherein a difference between glass transition temperature and crystallization initiation temperature in said bioactive glass is 80° C. or more, and wherein said composition forming said bioactive glass is free from $P_2O_5$.

14. A sintered calcium phosphate comprising a bioactive glass as a sintering aid, said bioactive glass formed from a composition consisting essentially of 30 to 60 mol % of CaO, 40 to 70 mol % of $SiO_2$, and at least one of $Na_2O$, $CaF_2$ and $B_2O_3$, $Na_2O$ being 0.1 to 5 mol %, $CaF_2$ being 0.1-1 mol %, and $B_2O_3$ being 5 mol % or less, wherein said sintered calcium phosphate is formed from a calcium phosphate comprising a hydroxyapatite, a carbonated apatite or tricalcium phosphate, and wherein said composition forming said bioactive glass is free from $P_2O_5$.

* * * * *